(12) United States Patent
Shepard et al.

(10) Patent No.: US 9,808,350 B2
(45) Date of Patent: Nov. 7, 2017

(54) LAMINOPLASTY IMPLANT, METHOD AND INSTRUMENTATION

(71) Applicant: Stryker European Holdings I, LLC, Kalamazoo, MI (US)

(72) Inventors: Yolanda D. Shepard, Hoboken, NJ (US); Charles L. Bush, Jr., Fairfield, NJ (US); Douglas Pedrick, Newburgh, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/030,496

(22) Filed: Sep. 18, 2013

(65) Prior Publication Data

US 2014/0067065 A1    Mar. 6, 2014

Related U.S. Application Data

(63) Continuation of application No. 13/362,413, filed on Jan. 31, 2012, now Pat. No. 8,562,681.

(51) Int. Cl.
*A61F 2/44* (2006.01)
*A61B 17/70* (2006.01)
*A61B 17/80* (2006.01)

(52) U.S. Cl.
CPC ............ *A61F 2/44* (2013.01); *A61B 17/7071* (2013.01); *A61B 17/808* (2013.01)

(58) Field of Classification Search
CPC ...... A61F 2/44; A61F 2/4405; A61B 17/7062; A61B 17/7071
USPC .............. 606/246–249, 99, 105, 86 A, 86 B; 623/17.11–17.16
See application file for complete search history.

(56) References Cited

U.S. PATENT DOCUMENTS

| | | | |
|---|---|---|---|
| 4,611,582 A | 9/1986 | Duff | |
| 4,997,432 A | 3/1991 | Keller | |
| 5,020,519 A | 6/1991 | Hayes et al. | |
| 5,176,702 A | 1/1993 | Bales et al. | |
| 5,209,755 A | 5/1993 | Abrahan et al. | |
| 5,250,056 A | 10/1993 | Hasson | |
| 5,304,203 A | 4/1994 | El-Mallawany et al. | |

(Continued)

FOREIGN PATENT DOCUMENTS

| | | |
|---|---|---|
| EP | 0923355 A1 | 6/1999 |
| EP | 1103236 A2 | 5/2001 |

(Continued)

OTHER PUBLICATIONS

Heller, J. and Wang, J., Centerpiece™ Plate Fixation System Surgical Technique, copyright 2005 Medtronic Sofamor Danek, Inc.

(Continued)

*Primary Examiner* — Ellen C Hammond
*Assistant Examiner* — Christina Negrellirodriguez
(74) *Attorney, Agent, or Firm* — Lerner, David, Littenberg, Krumholz & Mentlik, LLP

(57) ABSTRACT

In one embodiment, the present invention is a laminal implant including: a first body including a first flange adapted to engage a first lamina end, a tab and a receiving channel; and a second body including a second flange adapted to engage a second lamina end, and a plurality of teeth adapted to engage the tab, at least a portion of the second body adapted to be positioned within the receiving channel, the first and second bodies adapted to slideably engage one another.

16 Claims, 14 Drawing Sheets

(56) References Cited

U.S. PATENT DOCUMENTS

| | | |
|---|---|---|
| 5,672,177 A | 9/1997 | Seldin |
| 5,722,988 A | 3/1998 | Weisshaupt |
| 5,827,286 A | 10/1998 | Incavo et al. |
| 5,941,878 A | 8/1999 | Medoff |
| 5,964,763 A | 10/1999 | Incavo et al. |
| 5,980,572 A | 11/1999 | Kim et al. |
| 6,045,552 A | 4/2000 | Zucherman et al. |
| 6,080,157 A | 6/2000 | Cathro et al. |
| 6,126,660 A | 10/2000 | Dietz |
| 6,152,926 A | 11/2000 | Zucherman et al. |
| 6,183,471 B1 | 2/2001 | Zucherman et al. |
| 6,235,030 B1 | 5/2001 | Zucherman et al. |
| 6,238,397 B1 | 5/2001 | Zucherman et al. |
| 6,277,124 B1 | 8/2001 | Haag |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,358,254 B1 | 3/2002 | Anderson |
| 6,379,355 B1 | 4/2002 | Zucherman et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,478,800 B1 | 11/2002 | Fraser et al. |
| 6,500,178 B2 | 12/2002 | Zucherman et al. |
| 6,551,316 B1 | 4/2003 | Rinner et al. |
| 6,635,087 B2 | 10/2003 | Angelucci et al. |
| 6,660,007 B2 | 12/2003 | Khanna |
| 6,712,825 B2 | 3/2004 | Aebi et al. |
| 6,712,852 B1 | 3/2004 | Chung et al. |
| 6,796,983 B1 | 9/2004 | Zucherman et al. |
| 6,852,113 B2 | 2/2005 | Nathanson et al. |
| 6,893,464 B2 | 5/2005 | Kiester |
| 6,997,953 B2 | 2/2006 | Chung et al. |
| 7,087,055 B2 | 8/2006 | Lim et al. |
| 7,101,375 B2 | 9/2006 | Zucherman et al. |
| 7,169,153 B2 | 1/2007 | Keller |
| 7,189,234 B2 | 3/2007 | Zucherman et al. |
| 7,252,673 B2 | 8/2007 | Lim |
| 7,264,620 B2 | 9/2007 | Taylor |
| 7,288,103 B2 | 10/2007 | Suzuki |
| 7,294,134 B2 | 11/2007 | Weber |
| 7,326,216 B2 | 2/2008 | Bertagnoli et al. |
| 7,387,635 B2 | 6/2008 | Keller |
| 7,494,491 B2 | 2/2009 | Fankhauser et al. |
| 7,645,294 B2 | 1/2010 | Kalfas et al. |
| 7,651,500 B2 | 1/2010 | Supper et al. |
| 7,717,939 B2 | 5/2010 | Ludwig et al. |
| 7,749,231 B2 | 7/2010 | Bonvallet et al. |
| 7,803,162 B2 | 9/2010 | Marnay et al. |
| 7,867,237 B2 | 1/2011 | Stad et al. |
| 7,918,877 B2 | 4/2011 | Zucherman et al. |
| 8,105,366 B2 * | 1/2012 | Null ............... A61B 17/7071 606/246 |
| 8,172,875 B2 | 5/2012 | Taylor |
| 8,246,660 B2 | 8/2012 | Boris et al. |
| 8,926,664 B1 * | 1/2015 | Millhouse ......... A61B 17/7071 606/246 |
| 2002/0072752 A1 | 6/2002 | Zucherman et al. |
| 2002/0120335 A1 | 8/2002 | Angelucci et al. |
| 2002/0128654 A1 | 9/2002 | Steger et al. |
| 2003/0045935 A1 | 3/2003 | Angelucci et al. |
| 2003/0045936 A1 | 3/2003 | Angelucci et al. |
| 2003/0050700 A1 | 3/2003 | Kihara |
| 2003/0125738 A1 | 7/2003 | Khanna |
| 2003/0125740 A1 | 7/2003 | Khanna |
| 2003/0199875 A1 | 10/2003 | Mingozzi et al. |
| 2003/0225416 A1 | 12/2003 | Bonvallet et al. |
| 2004/0010251 A1 | 1/2004 | Pitaru et al. |
| 2004/0030388 A1 | 2/2004 | Null et al. |
| 2004/0153155 A1 | 8/2004 | Chung et al. |
| 2004/0210222 A1 | 10/2004 | Angelucci et al. |
| 2004/0220582 A1 | 11/2004 | Keller |
| 2005/0021042 A1 | 1/2005 | Marnay et al. |
| 2005/0055031 A1 | 3/2005 | Lim |
| 2005/0107877 A1 | 5/2005 | Blain |
| 2005/0119665 A1 | 6/2005 | Keller |
| 2005/0131412 A1 | 6/2005 | Olevsky et al. |
| 2005/0197700 A1 | 9/2005 | Boehm et al. |
| 2005/0251138 A1 | 11/2005 | Boris et al. |
| 2005/0273100 A1 | 12/2005 | Taylor |
| 2006/0025777 A1 | 2/2006 | Weber |
| 2006/0064091 A1 | 3/2006 | Ludwig et al. |
| 2006/0111712 A1 | 5/2006 | Jackson |
| 2006/0200134 A1 | 9/2006 | Freid et al. |
| 2007/0073185 A1 | 3/2007 | Nakao |
| 2007/0123907 A1 | 5/2007 | Weber |
| 2008/0009865 A1* | 1/2008 | Taylor ............................ 606/61 |
| 2008/0109005 A1 | 5/2008 | Trudeau et al. |
| 2009/0012527 A1 | 1/2009 | Mignucci et al. |
| 2009/0210012 A1 | 8/2009 | Null et al. |
| 2009/0281582 A1 | 11/2009 | Villa et al. |
| 2009/0306672 A1 | 12/2009 | Reindel et al. |
| 2010/0042217 A1 | 2/2010 | Zucherman et al. |
| 2010/0057127 A1* | 3/2010 | McGuire ...................... 606/246 |
| 2010/0063590 A1 | 3/2010 | Cannestra |
| 2010/0082029 A1 | 4/2010 | Ibrahim et al. |
| 2010/0114100 A1 | 5/2010 | Mehdizade |
| 2010/0114176 A1 | 5/2010 | Ibrahim et al. |
| 2010/0161056 A1 | 6/2010 | Voellmicke et al. |
| 2010/0185239 A1 | 7/2010 | Patel et al. |
| 2010/0185285 A1 | 7/2010 | Perkins |
| 2010/0191289 A1 | 7/2010 | Ludwig et al. |
| 2010/0241165 A1 | 9/2010 | Konieczynski et al. |
| 2010/0241230 A1 | 9/2010 | Mazzuca et al. |
| 2011/0046680 A1 | 2/2011 | Khanna |
| 2011/0106083 A1 | 5/2011 | Voellmicke et al. |
| 2011/0106084 A1 | 5/2011 | Gamache et al. |
| 2011/0106087 A1 | 5/2011 | Gamache |
| 2011/0106168 A1 | 5/2011 | Bucci et al. |
| 2011/0106169 A1 | 5/2011 | Zalenski et al. |
| 2012/0143339 A1 | 6/2012 | Voellmicke et al. |
| 2012/0165942 A1 | 6/2012 | Khanna |

FOREIGN PATENT DOCUMENTS

| | | |
|---|---|---|
| GB | 2381755 A | 5/2003 |
| JP | 63009434 A | 1/1988 |
| JP | 05103801 A | 4/1993 |
| JP | 08000638 A | 1/1996 |
| JP | 10179622 A | 7/1998 |
| JP | 11004840 A | 1/1999 |
| JP | 2000139970 A | 5/2000 |
| JP | 2000175943 A | 6/2000 |
| JP | 2001079024 A | 3/2001 |
| JP | 2001149392 A | 6/2001 |
| JP | 2001170092 A | 6/2001 |
| JP | 2005527315 A | 9/2005 |
| JP | 2011517420 A | 6/2011 |
| WO | 9709940 A1 | 3/1997 |
| WO | 9804217 A1 | 2/1998 |
| WO | 9921501 A1 | 5/1999 |
| WO | 9938461 A2 | 5/1999 |
| WO | 0044320 A1 | 8/2000 |
| WO | 0149220 A1 | 7/2001 |
| WO | 03002142 A1 | 1/2003 |
| WO | 03020141 A1 | 3/2003 |
| WO | 03101319 A2 | 12/2003 |
| WO | 2005096969 A1 | 10/2005 |
| WO | 2009120861 A2 | 10/2009 |
| WO | 2010144636 A1 | 12/2010 |
| WO | 2011010983 A1 | 1/2011 |
| WO | 2011040983 A1 | 4/2011 |

OTHER PUBLICATIONS

Partial Search Report for Application No. PCT/EP2013/051875 dated Apr. 15, 2013.

Patel et al., Part C Anterior Approach, Treatmetn of Cerfical Myelopathy, Ch. 76, pp. 1071-1080.

Shaffrey et al., "Modified open-door laminoplasty for treatment of neurological deficits in younger patients with congenital spinal

(56) References Cited

OTHER PUBLICATIONS stenosis: analysis of clinical and radiographic data," J. Neurosurg (Spine 2) vol. 90 (1999), pp. 170-177.
Yonenobu et al., Part B Laminoplasty, Treatment of Cerfical Myelopathy, Ch. 76, pp. 1057-1071.
European Search Report for EP Application 16157217.7 dated Aug. 3, 2016.

* cited by examiner

LAMINOPLASTY IMPLANT, METHOD AND INSTRUMENTATION

CROSS-REFERENCE TO RELATED APPLICATIONS

This application is a continuation of U.S. application Ser. No. 13/362,413, filed on Jan. 31, 2012, the disclosure of which is incorporated herein by reference.

BACKGROUND OF THE INVENTION

Spinal stenosis is a narrowing of the spinal canal, through which the spinal cord passes, that causes compression of the spinal cord. Such a narrowing can be caused by numerous factors including bone spurs, degeneration of the intervertebral disks and facet joints, and thickening of the ligaments. Among the symptoms spinal stenosis can produce are pain and/or numbness in the arms, clumsiness of the hands, and gait disturbances.

One such procedure for the repair of spinal stenosis is called a laminoplasty, in which the targeted vertebra is cut such that the vertebra can be spread apart to increase the diameter of the spinal canal. The cut produces two lamina ends, between which a laminoplasty plate is positioned to bridge the gap formed in the vertebra. Normally, a plate of an appropriate size is selected, bent to the desired shape and then fastened to the vertebra utilizing a plurality of screw holes positioned on the plate.

Two different laminoplasty procedures are in current use. The first is called the unilateral or "open door" laminoplasty in which one lamina (positioned to one side of the spinous process) is cut all the way through, while the other lamina (on the opposite side of the spinous process) is cut only partially through to create a hinge. The vertebral portion, including the spinous process, is then rotated about the hinge, and the plate is secured within the opening, maintaining the opening of the spinal canal.

The second procedure is called the bilateral or "French door" laminoplasty in which the midline of the spinous process is cut lengthwise all the way through, and each of the lamina are cut partially through to form two hinges. The bisected spinous process is then spread apart, and a plate is secured within the opening, again increasing the diameter of the spinal canal. Such laminoplasty procedures relieve pressure on the spinal cord while maintaining the stabilizing effects of the posterior elements of the vertebrae. By relieving pressure on the spinal cord it is the goal of laminoplasty to stop the progression of damage to the spinal cord and allow for a degree of recovery of function.

Commonly in "open door" laminoplasty procedures, the laminoplasty plate is of a solid construction having a rigid length to which the lamina ends must be positioned relative thereto. Alternatively the plate of an appropriate size is selected and bent to the desired shape and preferably has a plurality of screw holes, but again, such a plate has a rigid length. Adjustable length plates are also known in the art, though they are cumbersome and difficult to implant as they include multiple moving parts, all of which must be handled by a surgeon. Also, the accompanying instrumentation with such plates includes multiple handles which decrease the precision with which a surgeon can operate.

BRIEF SUMMARY OF THE INVENTION

Thus, there is a need in the art for an adjustable plate that can be easily expanded and include accompanying instrumentation which is simple to use and can perform the surgery by requiring minimal actions by the surgeon.

In one embodiment of the claimed invention, a laminal implant includes a first body and a second body, the first and second bodies being removeably coupled to one another and slidable relative to one another such that the implant may be expandable. The implant may further include a flange on an end of both the first and second bodies for engagement with first and second lamina ends of the vertebra. The implant may also include a tab on the first body and a plurality of teeth on the second body, wherein the tab and teeth may interact to allow unidirectional sliding of the first body relative to the second body. The teeth may be shaped such that they may pass the tab when moving in a first direction, but may be stopped from moving, by the tab, in a second direction opposite the first direction. The implant may further include at least one throughhole on each of the first and second bodies, adjacent the flanges, through which a fastener may be positioned to secure the implant to the lamina ends. The first and second bodies may also include a receiving channel on one of the bodies which may receive at least a portion of the body, such as a slide portion, therein. The receiving channel and slide interaction may form a track along which the first and second bodies may slide but still remain in proper alignment to one another.

In another embodiment, the present invention may include a laminal implant including a first body including a first flange adapted to engage a first lamina end, a tab and a receiving channel; and a second body including a second flange adapted to engage a second lamina end, and a plurality of teeth adapted to engage the tab, at least a portion of the second body adapted to be positioned within the receiving channel. The first and second bodies are adapted to slideably engage one another to expand or compress the implant. The first and second bodies may both also include an at least one through hole, through which a fastener may be positioned to provide further engagement, in addition to the flanges, to the lamina ends. Further, at least a portion of the flange of the first body may be pliable. The implant may further include at least one pin hole on each of the first and second bodies capable of interacting with an insertion instrument. Moreover, the first and second flanges may be adapted to engage at least two sides of each of the lamina ends. Additionally, the flange of the first body may be adapted to engage three sides of the first lamina end.

In a further embodiment, the present invention is a system for use in a laminoplasty procedure, the system including: an implant comprising a first body and a second body, the first and second bodies adapted to slide relative to one another to expand the implant; and an implantation instrument including: a shaft having a longitudinal length, a proximal end, a distal end and a hollow throughbore along at least a portion of its length; a handle positioned on the proximal end of the shaft; an actuator rod having a proximal portion and a distal portion, the actuator rod being positioned within the hollow throughbore of the shaft; a knob adapted to engage the proximal portion of the actuator rod; a first connector adapted to engage the distal portion of the actuator rod; and a second connector fixedly secured to the distal end of the shaft, wherein one of the first or second connectors is adapted to be removeably coupled to one of the first or second bodies, and the other of the first or second connectors is adapted to be removeably coupled to the other of the first or second bodies, wherein actuation of the knob slides at least one of the first or second bodies relative to the other.

Furthering this embodiment, the knob may be positioned adjacent to and proximal of the handle, and also the knob may be fixedly secured in a longitudinal position relative to the handle, but may be freely rotatable relative to the handle. The knob and actuator rod may also be coupled together through a threaded connection, such that the actuator rod is adapted to move longitudinally through the shaft by actuation of the knob. The first connector may also be adapted to actuate by the longitudinal movement of the actuator rod. For example, the first connector may include a slot within which may be positioned a tab extending from the actuator rod, wherein the tab may be adapted to travel within the slot by the longitudinal travel of the actuator rod. Moreover, the first connector may be pivotally connected to the shaft such that as the tab travels within the slot, the first connector pivots relative to the shaft, wherein the first connector may be adapted to pivot from an initial position substantially parallel to the second connector to a plurality of subsequent positions angled from the second connector. Furthermore, the first and second connectors each may include an attachment tip to removeably couple to a pin hole on each of the first and second bodies. The coupling of the attachment tip and pin hole may be a friction fit. Further, the actuator rod may be coaxial with the shaft. The first connector may also be actuable, through the actuator rod, by the knob.

In another embodiment of the claimed invention, an instrument for use with an implant in a laminoplasty procedure may include a handle, shaft, trigger and first and second jaws, the shaft extending from the handle, the trigger positioned adjacent to the handle, and the first and second jaws extending from the shaft opposite the handle, wherein one of the first or second jaws is capable of being removeably coupled to one of a first or second bodies of the implant, and the other of the first or second jaws is capable of being removeably coupled to the other of the first or second bodies, wherein actuation of the trigger moves the first and second jaws relative to one another, and thus, the first and second bodies of the implant relative to one another. The instrument may include a linkage between the first and second jaws such that rotational movement of the trigger may be translated into movement of the jaws such that the jaws remain parallel as they move relative to one another.

In a further embodiment, the present invention may include a method of performing a laminoplasty, the method including: removeably coupling an implant and an instrument, the implant comprising a first body and a second body, a flange on the first body and a flange on the second body, the first and second bodies being slidable relative to one another to expand the implant; advancing the implant to the laminoplasty site which includes first and second lamina ends; engaging one cut end with the flange of the first body and engaging the other cut end with the flange of the second body; expanding the implant using the instrument; decoupling the instrument from the implant; and fixedly securing the implant to the first and second lamina ends. The implant may be fixedly secured to the lamina ends through further engagement of the first and second flanges to the lamina ends through the placement of at least one fastener through each of the first and second bodies and into the lamina ends.

Alternatively, prior to the step of expanding the implant, fixedly securing the implant to one of the first or second lamina ends. Again, the implant may be fixedly secured to one of the lamina ends through further engagement of the first or second flange to the lamina end through the placement of at least one fastener through the first or second body and into the lamina end. In this embodiment, the implant may also be secured to the other lamina end subsequent to the step of decoupling the instrument from the implant.

DETAILED DESCRIPTION

Figure 12:
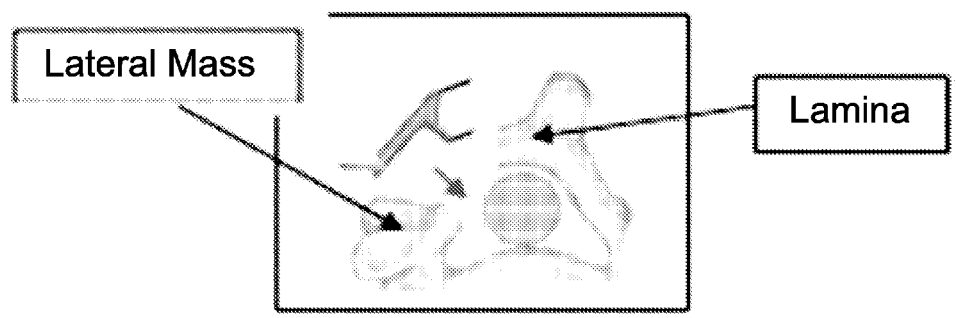
FIG. 12 illustrates one embodiment of the positioning of an implant of the present invention between lamina ends during the performance of a laminoplasty procedure.

The various embodiments of the present invention which will be discussed below will be discussed as if used in an "open door" laminoplasty (e.g., as in FIG. 12). However, the present invention is not intended to be limited to such a procedure as it is envisioned that the following implants, instrumentation, systems and methods may be used on other types of laminoplasty procedures and other spinal surgeries.

In a first embodiment, illustrated in FIGS. 1-4, the present invention includes an implant 10 including a first body 20 and a second body 30. The first and second bodies 20,30 each have a length, and the first and second bodies are removeably coupled to one another and slidable relative to one another, along their lengths, to expand or compress the implant.

Figure 1:
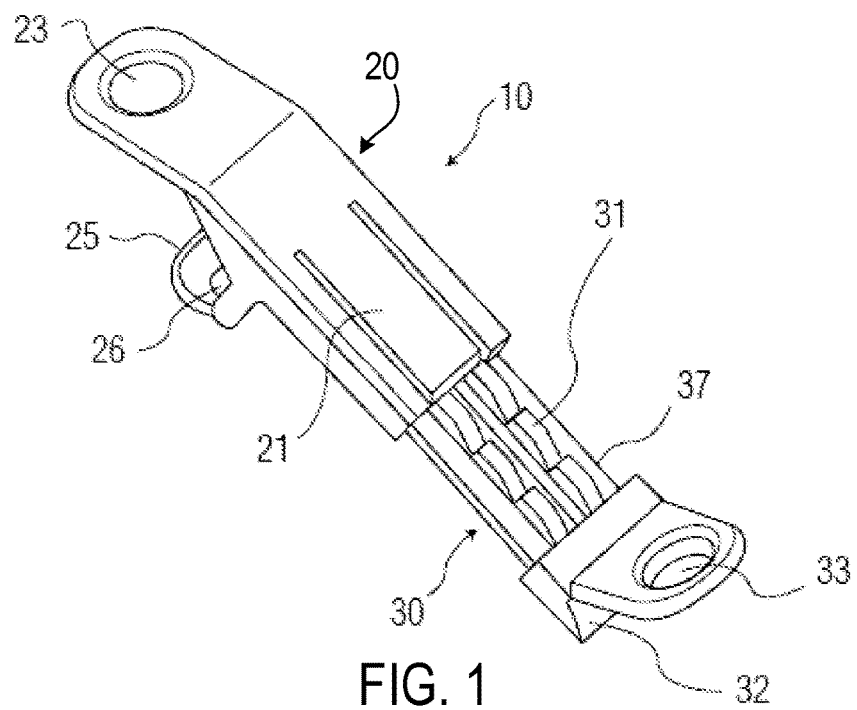
FIG. 1 illustrates a first embodiment of an implant including a first body and a second body.

The first body 20 includes a flange, such as for example a U-shaped saddle 25 as in FIG. 1, which engages up to three sides of one laminar cut end of the vertebra (e.g., outer side surface, inner side surface, and the cut edge surface). While the flange is sufficient to engage the implant with the laminar cut end, the flange may also include at least one through hole 23, through which a fastener (for example, see fastener 134 in FIG. 11B) may be passed to further engage the flange to the laminar cut end in a fashion to fixedly secure the implant to the lamina end. Suitable fasteners may be a bone screw, tack, pin, or other suitable structure commonly used in the spine. The flange may also include an opening 26, which results in the saddle 25 having less material than if saddle 25 were completely solid. The minimized material allows for the saddle 25 to have greater pliability. For example, the surgeon may be able to adjust the shape of the saddle 25, by bending the saddle or the like, to provide for a better fit onto the lamina end. Moreover, the opening 26 may optionally provide a location for placement of a bone graft or other osteogenic material, therethrough. The opening 26 may provide a window through which bone growth may occur, as well as serve to secure the bone graft in place while such bone growth takes place.

The second body 30 also includes a flange, such as for example a shoulder 32 as in FIG. 1, which is sized to engage up to two sides of the other lamina end of the vertebra (e.g., outer side surface and cut edge surface). While the flange is sufficient to engage the implant with the lamina end, the flange may also include at least one through hole 33, through which a fastener (for example, see fastener 134 in FIG. 11B) may be passed to further engage the flange to the lamina end in a fashion to fixedly secure the implant to the lamina end.

The first and second bodies 20,30 are slidable relative to one another, and thus each includes a structure to allow such a sliding arrangement. For example, as illustrated in FIGS. 1-4, the bodies may include a receiving channel 27 and an at least a portion of the other body adapted to be positioned within the channel 27, such as slide 37. Of course, the channel and slide could be transposed such that the channel is on the second body and the slide is on the first body; and likewise the first body could slide within the second body instead of the second body sliding within the first body, as illustrated.

Figure 2:
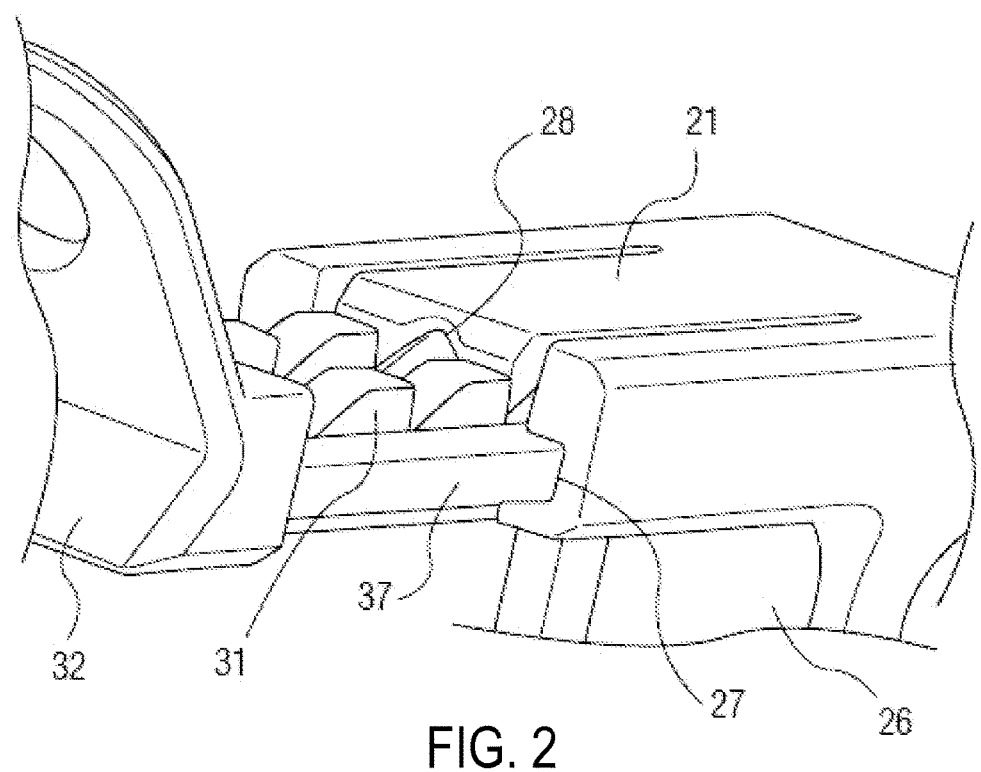
FIG. 2 illustrates a close-up view of the first body and the second body of the implant of FIG. 1.
Figure 3:
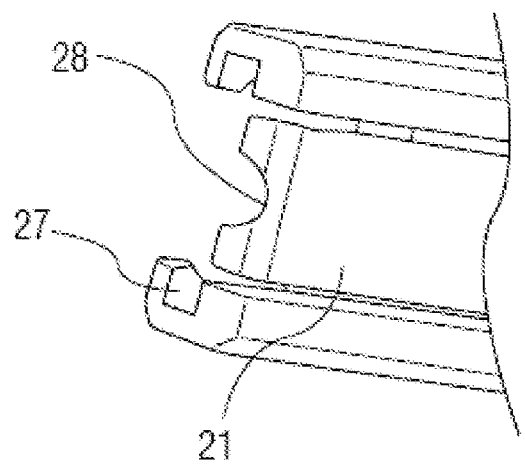
FIG. 3 illustrates a partial view of the second body of FIG. 7.
Figure 4:
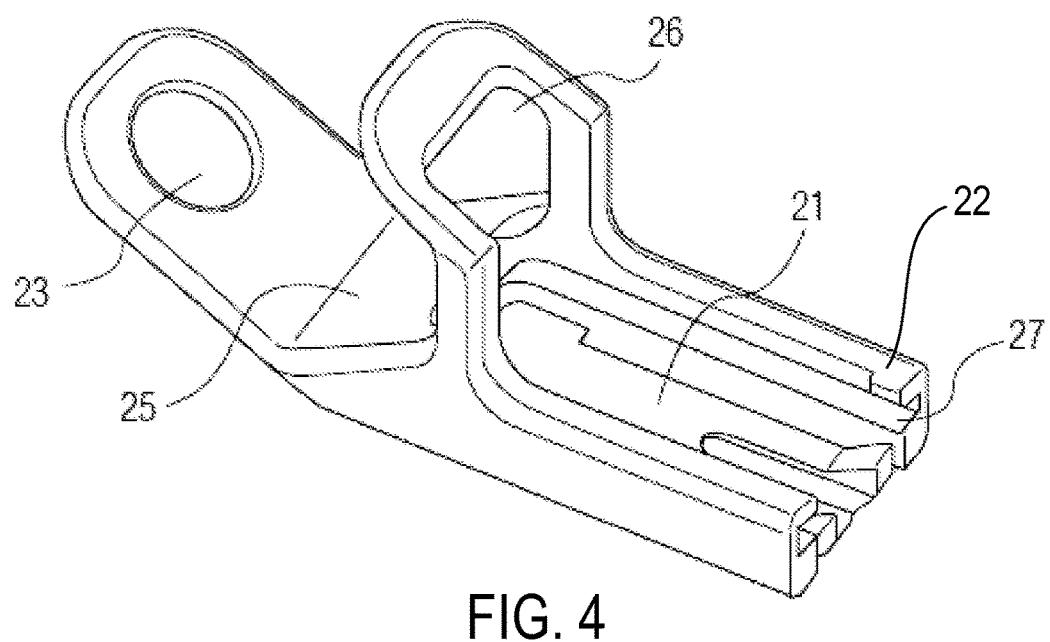
FIG. 4 illustrates a perspective view of the second body of FIG. 1.

The first and second bodies 20,30 further include cooperating structures which may secure the first and second bodies relative to one another to inhibit or otherwise control the sliding action. For example, as illustrated in FIGS. 1-4, the first body 20 includes a structure, along at least a portion of its length, for interacting with the second body such as, for example, a tab 21. The second body includes a structure which interacts with the structure on the first body (e.g., tab 21), such as for example a plurality of teeth 31. The tab 21 and teeth 31 may interact to allow unidirectional sliding of the first body relative to the second body. The teeth 31 may be shaped such that they may pass the tab when moving in a first direction, but may be prohibited from moving, by the tab 21, in a second direction opposite the first direction. For example, the tab 21 may be biased such that the tab 21 is resting at the base of the teeth. As a tooth passes under the tab, the tab deflects outwardly as an inclined face of the tooth passes under the tab, which allows the tooth to pass, but, the tab then returns to its original position once the tooth clears the tab. Of course, the tab will not deflect if the tooth attempts to pass the tab in the opposite direction since the shape of the tooth is inclined at an angle on only one side, and is generally perpendicular on the other side. A detailed view of such an arrangement is illustrated in FIG. 2.

Thus, for example, as will be discussed further below, the first and second bodies may slide away from one another to expand the length of the implant and thus expand the distance between the two lamina ends, and consequently, enlarge the diameter of the spinal canal. But, this arrangement prevents compression of the length of the implant, such that, once implanted and expanded to the desired length, the implant will maintain such length, and thus such expansion of the spinal canal. Tab 21 may be lifted or deflected manually by for example placing an appropriate instrument in access port 28, which would clear the tab from the teeth 31 and thus allow the first and second bodies to move bi-directionally since the teeth/tab interaction would no longer limit movement to only a single sliding direction. Lifting the tab may, using the embodiment illustrated, thus allow the first and second bodies to move towards one another and compress the length of the implant. This may be useful in the event of unintentional expansion of the implant prior to surgery, such that the surgeon can simply return the implant to its compressed position, using standard surgical instrumentation, in preparation for implantation into the spine. Alternatively, this may also be useful in the event of unintentional overexpansion of the implant once already implanted into the cut lamina.

Figure 6A:
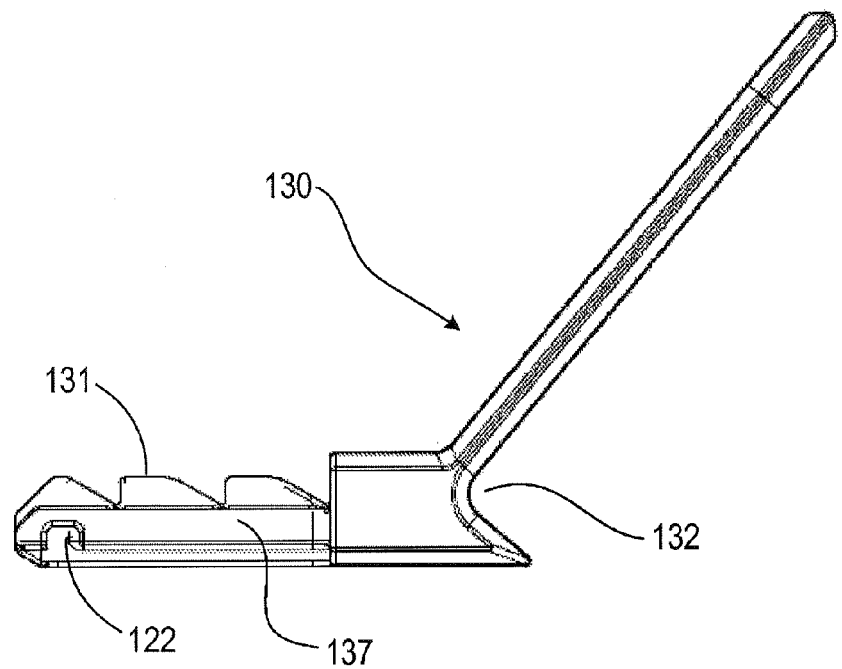
FIGS. 6A and 6B illustrate various views of the second body of the implant of FIG. 5.

The implant may further include a stop 22 which prevents the first and second bodies from being pulled completely apart. The stop 22 may be useful, for example, in preventing the surgeon from unintentionally pulling apart the implant in the midst of surgery, which would delay the surgery and cause an inconvenience to the surgeon. While the stop 22 is shown in one position, for example in FIG. 4, the stop may be positioned elsewhere on the implant so long as it substantially prevents the first and second bodies from being pulled apart (e.g., as in stop 122 in FIG. 6A).

Optionally, a bone graft or other bone-growth promoting (osteogenic) material may be positioned along at least a portion of the length of implant 10. For example, a bone graft may be placed through opening 26 and positioned along the length of the implant such that, over time, bone growth may occur from at least one of the lamina ends and through the bone graft. The opening 26 may stabilize the bone graft, while also allowing for uninhibited growth of bone through the opening 26 and between the lamina ends.

Figure 5:
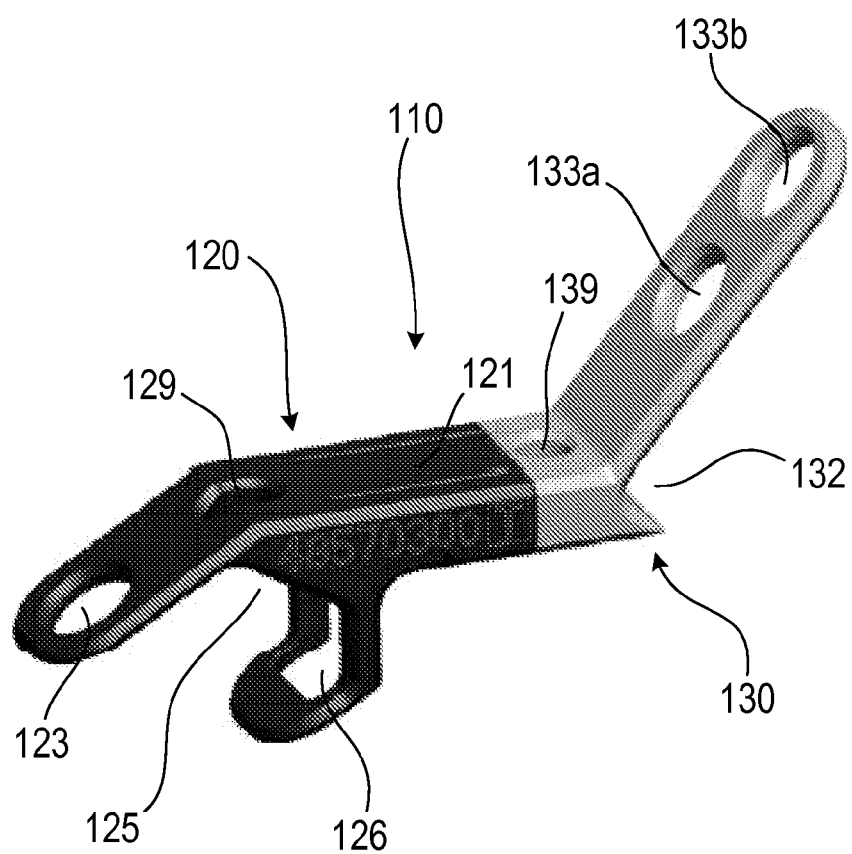
FIG. 5 illustrates another embodiment of an implant including a first body and a second body.
Figure 6B:
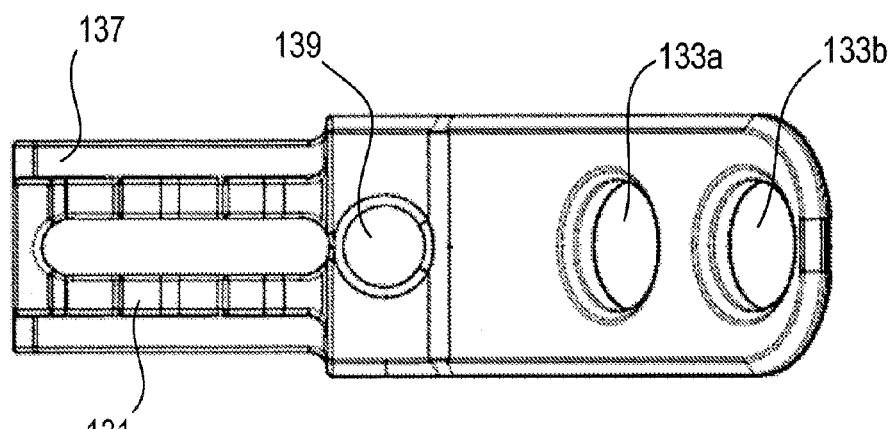
Figure 7A:
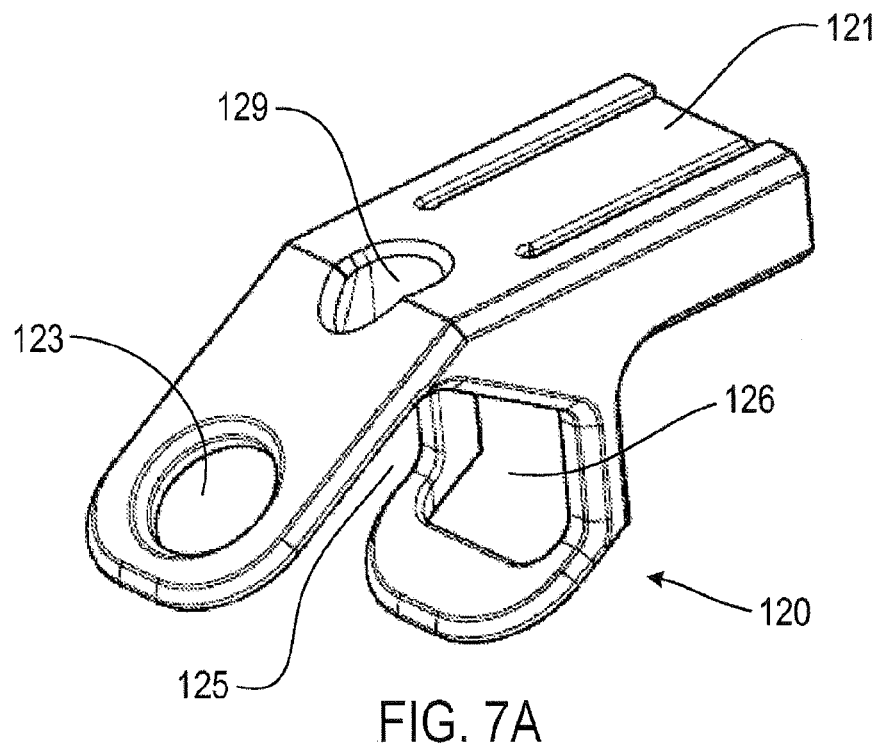
FIGS. 7A-7C illustrate various views of the first body of the implant of FIG. 5, including a perspective view of (7A) and cross-sectional views (7B, 7C).
Figure 7B:
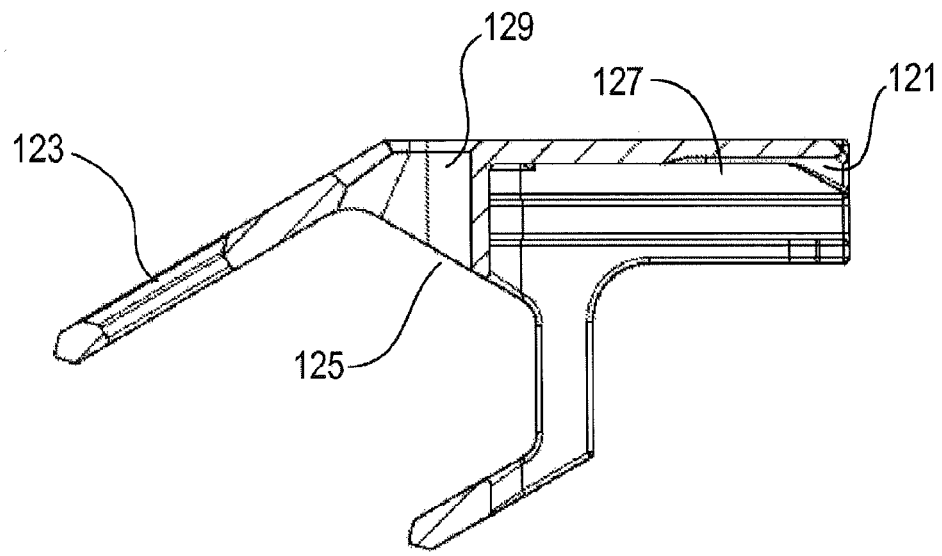
Figure 7C:
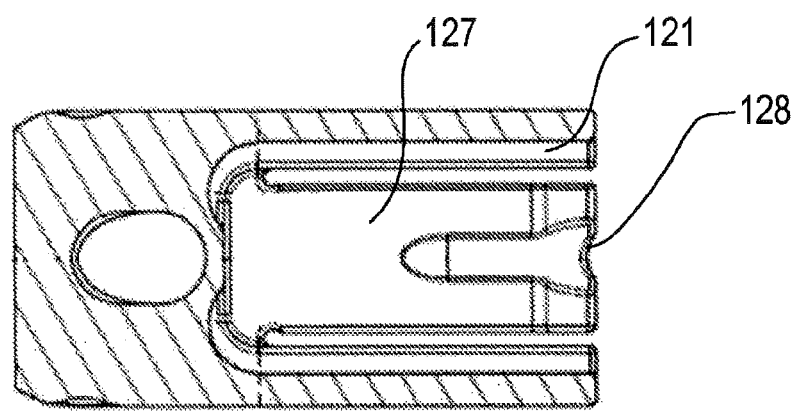

In another embodiment, the implant of the present invention may include, as illustrated in FIGS. 5-7, an implant 110 having a first portion 120 and a second portion 130. Implant 110 is similar in many respects to implant 10, and as such similar reference numbers (e.g., 20 vs. 120) refer to similar structures, except for certain differences, such as the following examples. First, implant 110 may further include pin holes 129,139 for interaction with an instrument (such as those described below) such that the instrument may engage and removeably couple the implant thereto. Second, body 130 may include two through holes 133a,133b for the placement of a second fastener (for example, see FIG. 11B) therethrough. Third, stop 122 may be positioned on body 130 rather than body 120.

While this embodiment includes pin holes 129,139 for interaction with the implantation instrument, other such interactive elements may be used. For example, as to the implant illustrated in FIG. 1, the instrument may have a forked grasping tip, or the like, which may be used to interact with the implant.

The implantation instrument of the present invention may be used for implantation of the implant, including at least holding, placement, expansion and release of the implant between lamina ends within a cut lamina of a spine.

Figure 8A:
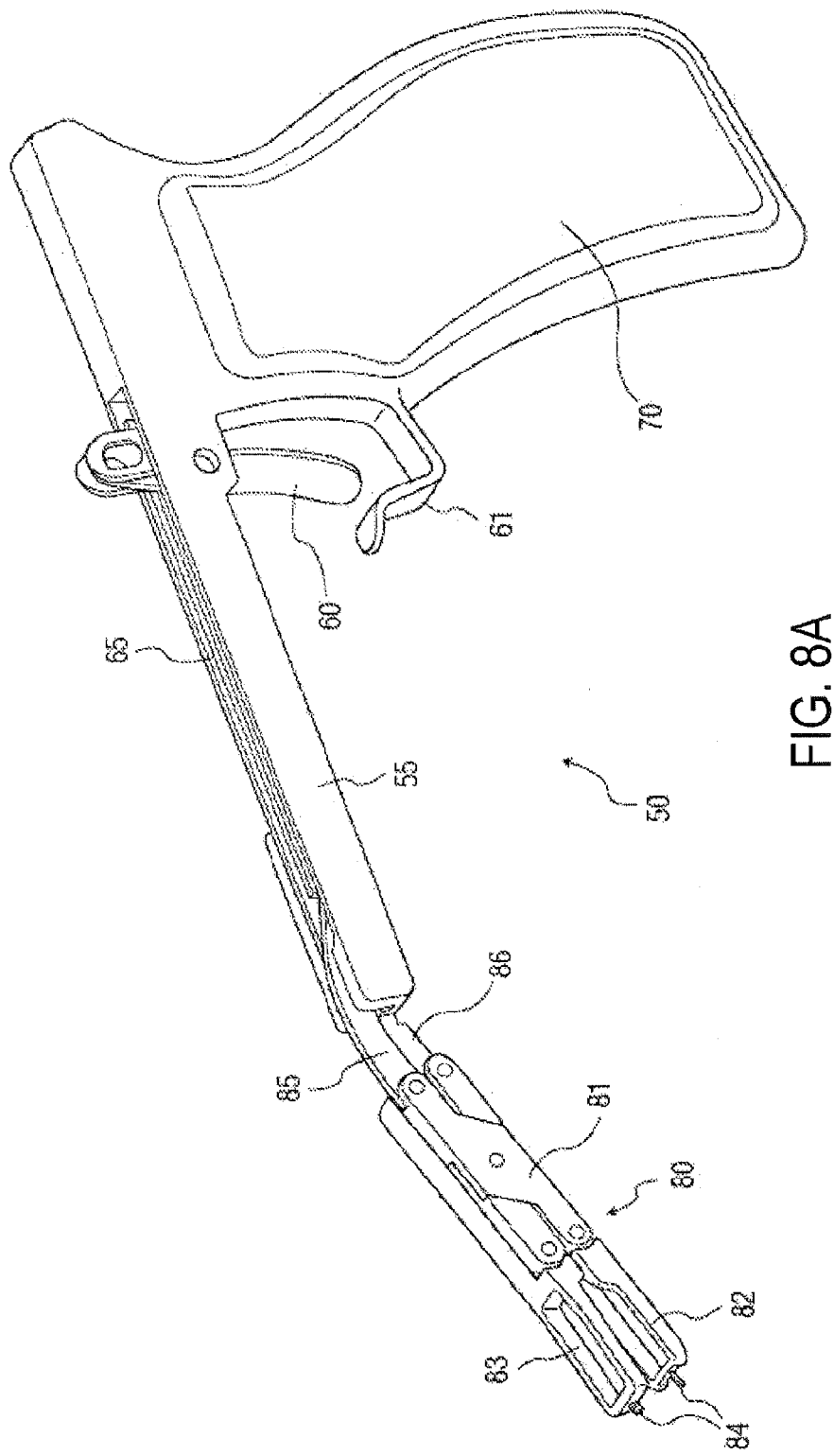
FIGS. 8A, 8B and 9 illustrate one embodiment of an instrument of the present invention, and FIG. 9 also includes the implant of FIGS. 1-4 removeably coupled thereto.
Figure 8B:
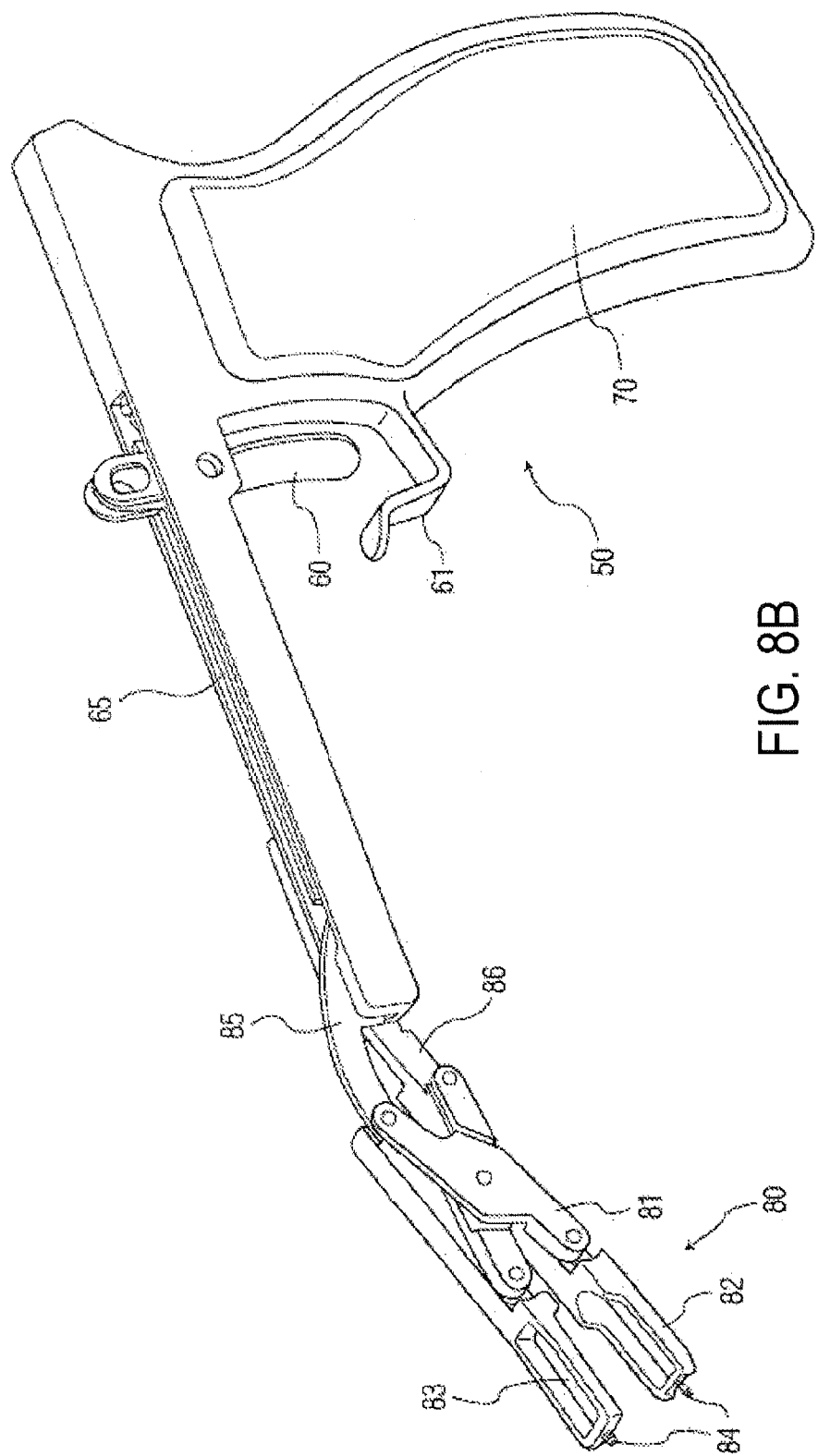
Figure 9:
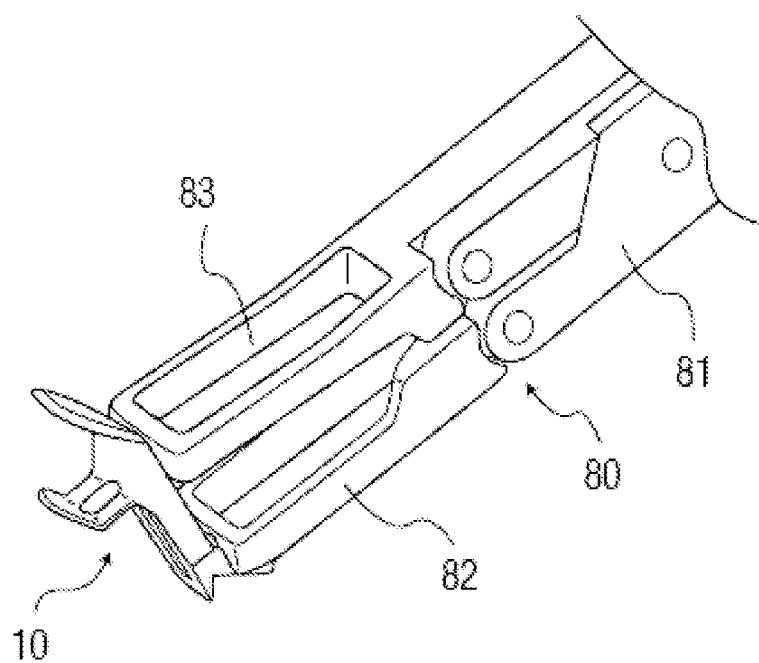

In one embodiment, illustrated in FIGS. 8A, 8B and 9, the present invention includes an implantation instrument 50 which includes a shaft 55 extending between a handle 70 at a proximal end and a distal end 80. The instrument further includes an actuation mechanism which allows the surgeon to manipulate the distal end 80. As illustrated in the exemplary embodiment of FIGS. 8A, 8B and 9, the actuation mechanism may include a trigger 60 and actuator rod 65. In this embodiment, the rotational movement of trigger 60, when depressed or released by the surgeon's finger, is translated into linear longitudinal movement of actuator rod 65, which then imparts this movement onto the distal end 80. The handle 70 may also include a trigger guard 61 to assist in preventing unintentional actuation of the trigger. The actuator rod 65 may further include a ratchet mechanism which may provide improved control of movement as well as provide an ability of the surgeon to maintain a desired position.

Continuing with this embodiment, the distal end 80 may include first and second jaws 82,83, each having an attachment tip 84 for connection to implant 10 (as in FIG. 9). The jaws 82,83 may be connected to one another through a linkage 81, which is in turn connected to the shaft via a connecting link 86 and to actuator rod 65 via banana link 85. Such a series of connections may cause the jaws 82,83, through actuation of the trigger 60, to move towards or away from one another, and consequently, when the implant 10 is secured to the instrument 50, to cause the first and second bodies 20,30 to slide relative to one another. As illustrated, the distal end 80 is positioned at an angle relative to the shaft 55. This angle may be any desired angle, and may even be about 0 degrees such that the distal end is substantially linear to the shaft. This angle as illustrated, though, may provide improved use by the surgeon in providing a better angle of entry and line of sight to the surgical space, as well as provide better transfer of force from the trigger, to the actuator rod, to the distal end.

This movement of the jaws 82,83, as to this embodiment, is obtained as follows. Trigger 60 may have a default or biased position, though such a position is not required. If a biased positioned is included, typically a spring or other mechanism may be included to tension the trigger towards one position. In FIG. 8A, for example, the trigger 60 may be tensioned in the forward position, such that the default or biased position places the jaws 82,83 close together (and thus, if implant 10 is attached to the jaws, the implant would be in a default compressed configuration, as in FIG. 9). Biasing the trigger in this fashion may also provide for some resistance on the trigger when the surgeon depresses it, which may provide added control for the surgeon. This biasing also improves the ability of the instrument to hold the implant 10 due to the compression of the implant between the jaws.

As the trigger 60 is depressed, or pulled rearwards towards the handle 70, the trigger pivots and forces the actuator rod 65 forwards, towards the distal end 80. This forward motion places a forward force on the banana link 85. However, the linkage 81 is held in place relative to the shaft 55 by connecting link 86. Thus, as shown in FIG. 8b, the forward motion of the actuating rod 65 causes the banana link 85 to rotate and expand linkage 81, since the linkage 81 is prohibited from moving forward. As the linkage 81 expands, the jaws 82,83 move apart and expand the space between them. However, due to the connecting link and linkage interaction, the jaws do not change orientation relative to one another (they remain substantially parallel to one another) or move laterally closer or farther from the rest of the instrument. Thus, as will be discussed further below, the linkage configuration may allow the surgeon to place the implant 10 in position on the vertebra and then expand the implant 10, while keeping it in position on the vertebra. The surgeon does not have to account for additional movement of the implant as the trigger is depressed, such as rotational movement, lateral movement, or the like, because the linkage configuration translates depression of the trigger into unidirectional expansion of the implant.

The instrument 50 can act as a holder of the implant, as illustrated in FIG. 9. The trigger 60 may be spring biased in a closed position to provide better securement of the implant 10. The instrument can also act as an expander for the implant in conjunction with holding the implant. Of course, when an implant is connected to the jaws, and the implant is expanded when positioned on and between two lamina ends, the instrument will perform both an expansion of the implant and, consequently, an expansion of the space between the two lamina ends as well as an expansion of the spinal canal.

In a further embodiment, as illustrated again in FIG. 9, the present invention includes a system including an implant 10 and an instrument 50. The implant 10 is expandable or compressible and includes a first body 20 and a second body 30, the first and second bodies being slidable relative to one another to expand or compress the implant. The instrument 50 includes a handle 70, shaft 55, trigger 60 and first and second jaws 82,83, the shaft extending from the handle, the trigger positioned adjacent to the handle, and the first and second jaws positioned on the shaft opposite the handle, wherein one of the first or second jaws is capable of being removeably coupled to one of the first or second bodies 20,30, and the other of the first or second jaws is capable of being removeably coupled to the other of the first or second bodies 20,30, wherein actuation of the trigger moves the first and second jaws relative to one another. As the jaws move relative to one another, the first and second bodies of the implant may also slidably move relative to one another. The implant 10 is press-fit, or otherwise removably connected, to the jaws 82,83 on attachment tips 84.

Figure 10A:
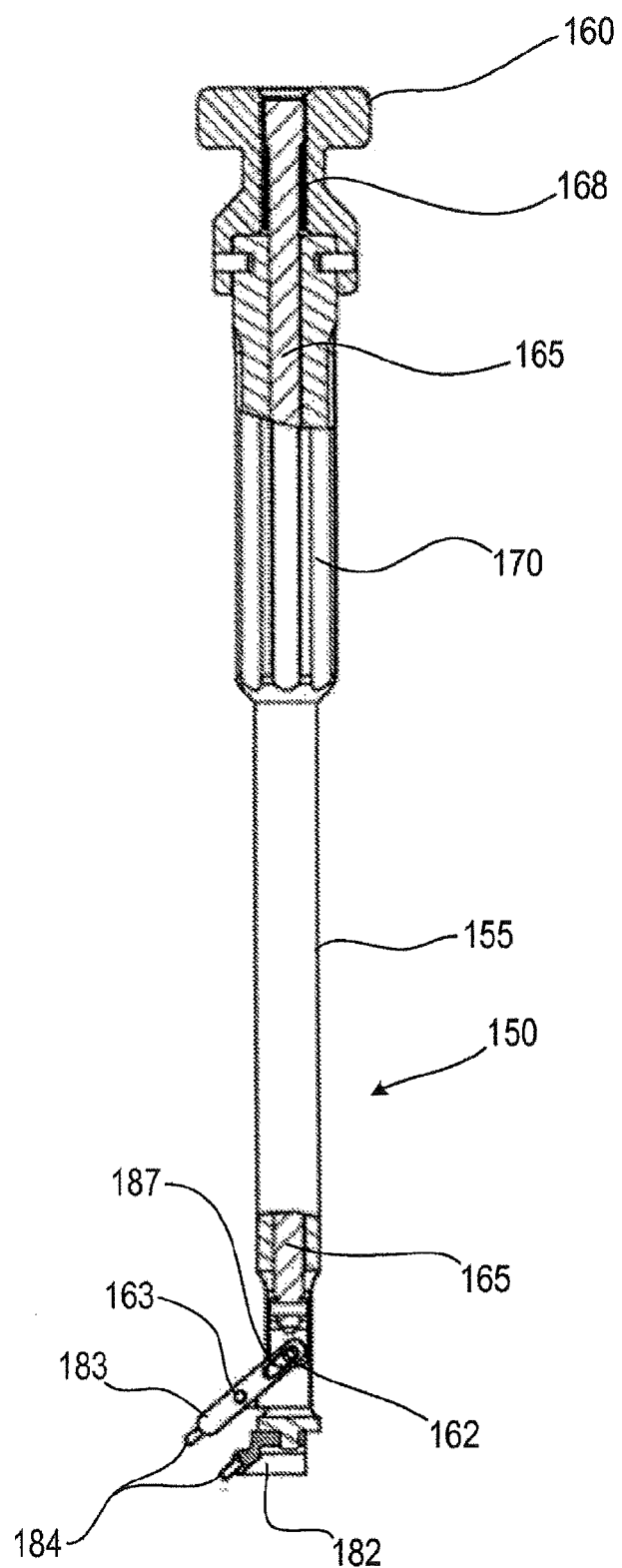
FIGS. 10A and 10B illustrate another embodiment of an instrument of the present invention to which an implant of the present invention may be removeably coupled thereto.
Figure 10B:
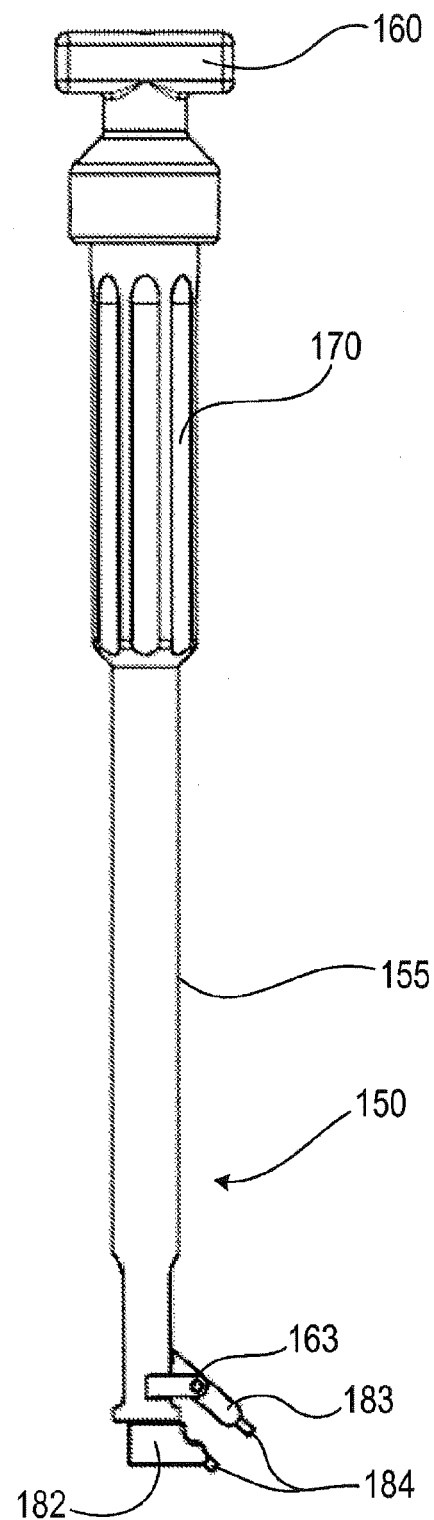

FIGS. 10A and 10B illustrate a further embodiment of an implantation instrument 150. In this embodiment, instrument 150 includes a shaft 155 having a length and proximal and distal ends. Shaft 155 is also hollow along at least a portion of its length to accommodate an actuator rod 165 therethrough. In the illustrative example, the shaft 155 is hollow along its entire length. The instrument 150 also includes a handle 170 positioned along the proximal portion of the shaft 155. The handle and shaft may be fixedly secured to one another or, alternatively, the handle and the shaft may be manufactured as a single, monolithic structure.

The actuator rod 165 has a proximal portion and a distal portion, and a knob 160 is adapted to engage the proximal portion of the actuator rod. Knob 160, as illustrated, may be positioned adjacent to and proximally of the handle 170. Knob 160 may also be fixedly secured in a longitudinal position relative to the handle 170, but may be freely rotatable relative to the handle. This freedom of rotation permits the actuation of knob 160, through rotation around the longitudinal length of the instrument, and thereby cause linear or longitudinal movement of the actuator rod 165 through the shaft 155, as the actuator rod 165 and shaft 155 may be coaxial with one another. The translation of rotational motion of the knob 160 to longitudinal movement of the actuator rod 165 may be accomplished through the coupling of the two elements by a threaded connection 168. As will be discussed below, actuation of the knob slides at least one of the first or second bodies 120, 130 of implant 110 relative to the other.

The instrument 150 also includes a first connector 183 and a second connector 182, wherein one of the first or second connectors is adapted to be removeably coupled to one of the first or second bodies 120, 130, and the other of the first or second connectors is adapted to be removeably coupled to the other of the first or second bodies 120, 130. As illustrated, the first connector 183 is adapted to engage the distal portion of the actuator rod 165, while the second connector 182 is fixedly secured to the distal end of the shaft 155.

The first connector 183 may be adapted to actuate by the longitudinal movement of the actuator rod 165 created by the actuation of knob 160. For example, as illustrated in this embodiment, the first connector 183 may include a slot 187 within which may be positioned a tab 162 extending from the actuator rod 165, wherein the tab 162 may be adapted to travel within the slot 187 as coordinated by the longitudinal travel of the actuator rod 165 through the shaft. Moreover, the first connector 183 may be pivotally connected to the shaft 155 such that as the tab 162 travels within the slot 187, the first connector pivots relative to the shaft, wherein the first connector may be adapted to pivot from an initial position substantially parallel to the second connector 183 (as in FIGS. 10A, 10B) to a plurality of subsequent positions angled from the second connector. This pivot may occur around pivot pin 163 which extends from and is fixedly secured with shaft 155.

The second connector 182 is fixedly secured to the shaft 155, and as such the first or second body 120, 130, whichever is removeably coupled to the second connector 182, is also held in place relative to the shaft 155. Thus, in use, as the first connector 183 pivots, as explained above, the first or second body 120, 130 removeably coupled to first connector 183 will likewise move with first connector 183 and slide relative to the other body 120, 130 removeably coupled to the second connector 182.

Each of the first and second connectors may include an attachment tip 184 to removeably couple to a pin hole 129,139 on each of the first and second bodies 120, 130. The coupling of each attachment tip and pin hole may be a friction fit or the like.

This embodiment of the implantation instrument 150 may also be combined with an implant, such as implant 110, to form a system including instrument 150 and at least one implant 110. The system, for use in a laminoplasty procedure, includes an implant 110 comprising a first body 120 and a second body 130, the first and second bodies adapted to slide relative to one another to expand or compress the implant, and an implantation instrument 150 including: a shaft 155 having a longitudinal length, a proximal end, a distal end and a hollow throughbore along at least a portion of its length; a handle 170 positioned on the proximal end of the shaft; an actuator rod 165 having a proximal portion and a distal portion, the actuator rod 165 being positioned within the hollow throughbore of the shaft 155; a knob 160 adapted to engage the proximal portion of the actuator rod; a first connector 183 adapted to engage the distal portion of the actuator rod; and a second connector 182 fixedly secured to the distal end of the shaft, wherein one of the first or second connectors is adapted to be removeably coupled to one of the first or second bodies, and the other of the first or second connectors is adapted to be removeably coupled to the other of the first or second bodies, wherein actuation of the knob slides at least one of the first or second bodies relative to the other.

Furthering this embodiment, the knob 160 may be positioned adjacent to and proximal of the handle 170, and also the knob 160 may be fixedly secured in a longitudinal position relative to the handle 170, but may be freely rotatable relative to the handle. The knob 170 and actuator rod 165 may also be coupled together through a threaded connection 168, such that the actuator rod is adapted to move longitudinally through the shaft by actuation of the knob. The actuator rod 165 may be coaxial to the shaft 155. The first connector 183 may also be adapted to actuate by the longitudinal movement of the actuator rod, via the actuation of the knob 160. In one embodiment, the first connector may include a slot 187 within which may be positioned a tab 162 extending from the actuator rod, wherein the tab may be adapted to travel within the slot by the longitudinal travel of the actuator rod. Moreover, the first connector may be pivotally connected to the shaft, at pivot pin 163 extending from the shaft, such that as the tab travels within the slot, the first connector pivots relative to the shaft, wherein the first connector may be adapted to pivot from an initial position substantially parallel to the second connector to a plurality of subsequent positions angled from the second connector. Furthermore, the first and second connectors each may include an attachment tip 184 to removeably couple to a pin hole 129,139 on each of the first and second bodies. The coupling of the attachment tip and pin hole may be a friction fit.

In use, the system is capable to adjusting the implant 110 from, for example, a compressed position (as in FIG. 5) to an expanded position (as implant 10 is presented in FIG. 1) through the actuation of the knob 160. Thus, in this embodiment, once the implant was in place and engaged to the lamina ends (discussed below), a surgeon may, holding the handle 170 substantially steady to minimize or prevent its rotation, rotate the knob 160 which thereby rotates the knob relative to the actuator rod 165 at threaded connection 168. The rotation of the knob forces the actuator rod 165 to move longitudinally which, in this embodiment, would be distally, towards the first connector 183. The actuator rod 165 moves distally as a result of the threaded connection 168 because the actuator rod may be inhibited from rotating along with the knob, by for example pin 162 or by another similar structure, such that the threading of the knob instead travels along the thread of the actuator rod. As the actuator rod 165 moves distally, tab 162 also moves distally, thereby forcing the portion of the first connector including the slot 187 also distally. As the first connector is affixed by pivot pin 163, the distal motion of the slot 187 causes generally proximal movement of the other end of the first connector 183, which includes the attachment tip 184. Thus, as the attachment tip 184 of the first connector 183 moves proximally, it moves away from the attachment tip 184 of the second connector 182, thereby increasing the distance between the two connectors. Of course, since the implant 110 is removeably coupled to the first and second connectors, the first and second bodies 120,130 of the implant also slide apart, thereby expanding the implant. Since the implant is positioned and engaged to the lamina ends, the expansion of the implant also expands the spinal canal and the distance between the lamina ends.

Figure 11A:
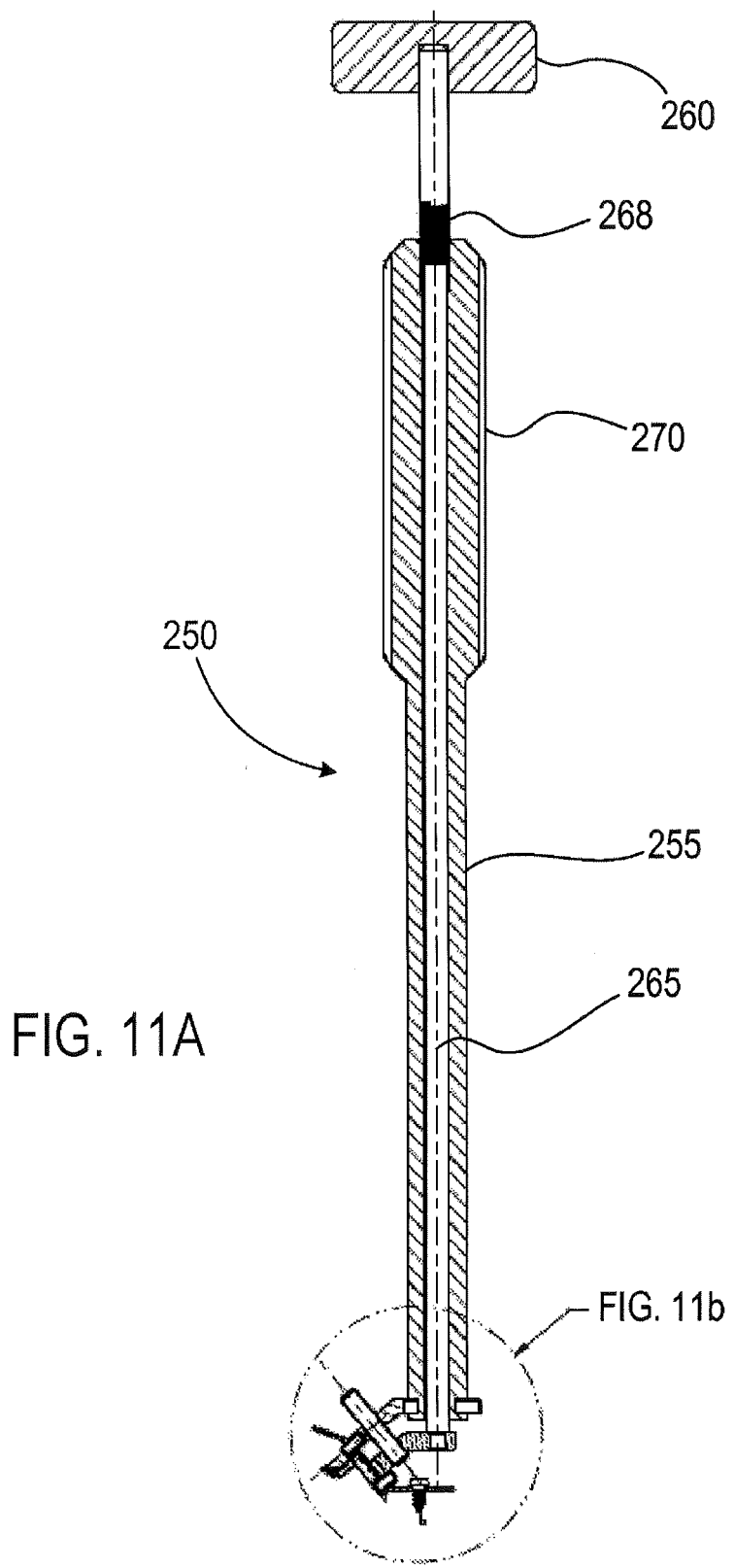
FIGS. 11A and 11B illustrate yet another embodiment of an instrument of the present invention, also including the implant of FIGS. 5-7 removeably coupled thereto.
Figure 11B:
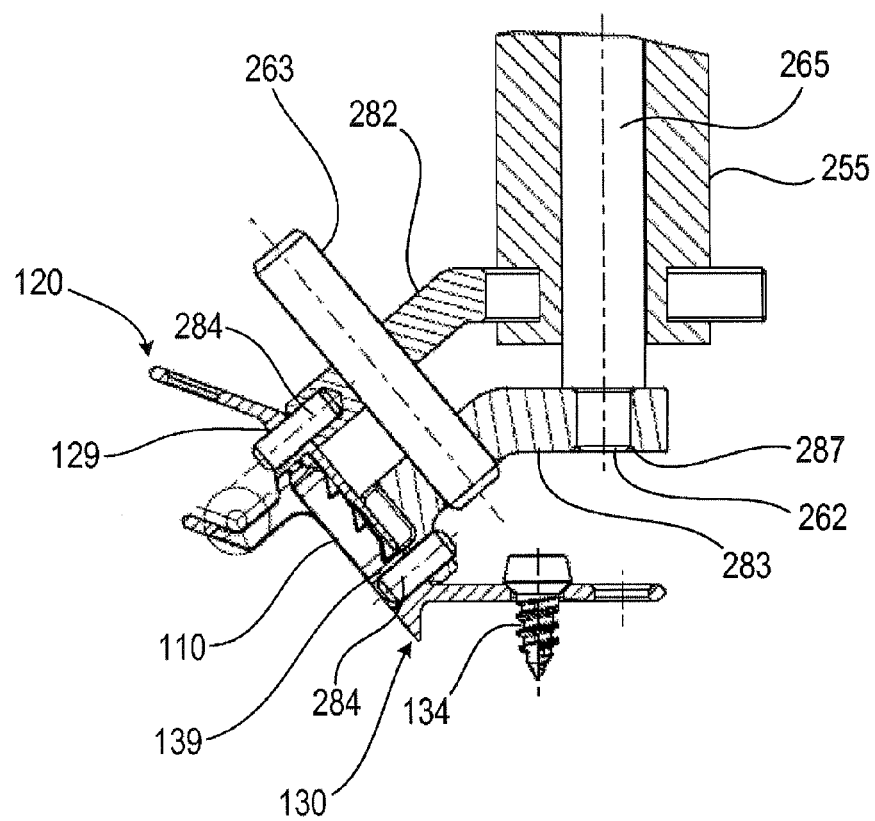

FIGS. 11A and 11B illustrate yet another embodiment of the present invention, namely, an instrument 250 including a shaft 255 having a longitudinal length, a proximal end, a distal end and a hollow throughbore along at least a portion of its length. The hollow throughbore accommodates an actuator rod 265 therethrough. In the illustrations, the shaft 255 is hollow along its entire length. The instrument also includes a handle 270 positioned along the proximal portion of the shaft 255. The handle and shaft may be fixedly secured to one another or, alternatively, the handle and the shaft may be manufactured as a single, monolithic structure.

The actuator rod 265 has a proximal portion and a distal portion, and a knob 260 is adapted to fixedly engage the proximal portion of the actuator rod. Knob 160, as illustrated, may be positioned proximally of the handle 170. The knob 160 and actuator rod 265, being fixedly engaged thereto, are freely rotatable relative to the handle 270 and shaft 255. The actuator rod 265 and shaft/handle may be coaxial and further coupled together via a threaded connection 268. This freedom of rotation permits the actuation of knob 260, through rotation around the longitudinal length of the instrument, and thereby causes linear or longitudinal movement of the actuator rod 265 relative to and through the shaft 255. Thus, the threaded connection 268 accomplishes the translation of rotational movement of the knob and actuator rod into longitudinal movement relative to the shaft 255. As will be discussed below, actuation of the knob slides at least one of the first or second bodies 120,130 of implant 110 relative to the other.

The instrument 250 also includes a first connector 283 and a second connector 282, wherein one of the first or second connectors is adapted to be removeably coupled to one of the first or second bodies 120,130, and the other of the first or second connectors is adapted to be removeably coupled to the other of the first or second bodies 120,130. As illustrated, the first connector 283 is adapted to engage the distal portion of the actuator rod 265, while the second connector 282 is fixedly secured to the distal end of the shaft 255.

The first connector 283 may be adapted to actuate by the longitudinal movement of the actuator rod 265 created by the actuation of knob 260. For example, as illustrated in this embodiment, the first connector 283 may include a bore 287 within which a tab 262, extending from actuator rod 265, may be rotatably coupled, such that as the actuator rod 265 rotates and moves longitudinally (and distally), the tab 262 freely rotates within bore 287 while imparting longitudinal force on the first connector 283 to move the first connector distally. The first connector may be prevented from rotating by pin 263, which prevents rotation of the first connector while still allowing the longitudinal movement of the first connector caused by the actuator rod 265.

The second connector 282 is fixedly secured to the shaft 255, and as such the first or second body 120, 130 which is removeably coupled to the second connector 282 is also held in place relative to the shaft 255. Thus, in use, as the first connector 283 moves distally, as explained above, the first or second body 120,130 removeably coupled thereto will slide relative to the body 120, 130 removeably coupled to the second connector 282.

Each of the first and second connectors may include an attachment tip 284 to removeably couple to a pin hole 129, 139 on each of the first and second bodies 120, 130. The coupling of each attachment tip and pin hole may be a friction fit.

As illustrated in FIGS. 11A and 11B, this embodiment of the implantation instrument 250 may also be combined with an implant, such as implant 110, to form a system including instrument 250 and at least one implant 110. In use, the system is capable to adjusting the implant 110 from, for example, a compressed position (as in FIG. 11B) to an expanded position (as implant 10 is presented in FIG. 1) through the actuation of the knob 260. Thus, in this embodiment, once the implant was in place and engaged to the lamina ends (discussed below), a surgeon may, holding the handle 270 substantially steady to prevent its rotation, rotate the knob 260 which thereby rotates the actuator rod 265 relative to the shaft 255 at threaded connection 268. The rotation of the knob forces the actuator rod 265 to rotate and move longitudinally (on account of the threaded connection 268) which, in this embodiment, would be distally, towards the first connector 283. The actuator rod 265 moves distally as a result of the threaded connection 268 because the actuator rod rotates relative to the shaft and handle while the shaft and handle are prevented from rotating by the surgeon (e.g., by holding the handle). As the actuator rod 265 moves distally, tab 262 also moves distally, thereby forcing the first connector also distally. As the first connector is affixed by pin 263, tab 262 rotates freely within bore 287, and thus the first connector does not rotate along with tab 262. The first connector does move distally, though, along with attachment tip 284. As first connector and attachment tip 284 move distally, they move away from the second connector 282 and attachment tip 284 of the second connector, such that the distance between the two connectors, and two attachment tips, increases. Of course, since the implant 110 is removeably coupled to the first and second connectors, the first and second bodies 120,130 of the implant also slide apart, thereby expanding the implant. Since the implant is positioned and engaged to the lamina ends, the expansion of the implant also expands the spinal canal and the distance between the lamina ends.

In another alternative embodiment, the present invention may include a kit including one of the above instruments and a plurality of implants which may be used on multiple vertebrae in a single patient or in multiple patients in subsequent surgeries. Alternatively, the kit may include implants of various dimensions and sizes such that the surgeon may select the properly sized implant for the specific patient and type of vertebra. Then, the implant may be expanded, from a compressed configuration, to fine tune the implant length for the specific application.

The various implants, instruments, systems and kits of the present invention may be sterilized and packaged from the manufacturer as a combined system, such that the system can be removed from the packaging and immediately used in a surgery. Alternatively, the system may include an individually packaged implant and an instrument which may be sold and packaged separately. Additionally, the various instruments may be sterilizable and reusable in subsequent surgeries.

The various disclosed embodiments of the implant and instrument of the present invention may be used in various methods of surgery. While it is envisioned that any of the instruments may be used with the implant embodiments disclosed, the below discussion of exemplary methods will use the implant of FIGS. 5-7 and the instrument of FIGS. 10a and 10b for illustrative purposes.

In one embodiment, the method of performing a laminoplasty includes removeably coupling an implant and an instrument, the implant including a first body and a second body, a flange on the first body and a flange on the second body, the first and second bodies being slidable relative to one another to expand or compress the implant. For example, this step may include removeably coupling implant 110 to instrument 150, by attaching attachment tips 184 to pin holes 129, 139, with the implant 110 in a substantially compressed configuration, such that the first and second connectors 183, 182 may be generally parallel to one another. Next, the implant is advanced to the laminoplasty site which includes first and second lamina ends, as illustrated, for example, in FIG. 12. The implant is then positioned to engage one cut end with the flange of the first body and engaging the other cut end with the flange of the second body, and expanding the implant using the instrument. The implant is then decoupled from the instrument. At this point, the implant may be substantially secured within the lamina. However, to ensure the implant remains in place and in a proper orientation relative to the vertebra, the implant may be fixedly secured to the lamina ends through further engagement of the first and second flanges to the lamina ends through the placement of at least one fastener through each of the first and second bodies and into the lamina ends.

In another embodiment of the present invention, the method of performing a laminoplasty may be similar to the above method however, prior to the step of expanding the implant, the implant is fixedly secured to one of the lamina ends using a fastener (such as fastener 134 of FIG. 11B). For example, a fastener may be placed through at least one of throughbores 123, 133a or 133b, after the flanges of the first and second bodies have engaged the lamina ends. The implant may then be expanded, as necessary, using the instrument. The implant is then decoupled from the instrument. Finally, additional fasteners are applied in the other through bores of the implant (e.g., through bores 123 and the other of 133a or 133b) to fixedly secure the implant to the first and second lamina ends.

In yet a further embodiment, a method of the present invention may include steps similar to those above, however, the instrument 150, for example, may be coupled to the implant after the implant is in place on the lamina ends. In this embodiment, alternative instrumentation may be used to place the implant onto the lamina ends. For example, a pair of forceps or the like may be used to move the implant into position. A second instrument, such as a grasper or the like may pry the cut ends of the lamina apart. Once the lamina ends are expanded, the forceps are used to move the implant into position onto the lamina ends. The grasper and forceps are then withdrawn from the surgical site and instrument 150 is then secured to the implant, along with at least one fastener to further secure the implant to at least one of the lamina ends. The method then continues as discussed above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A laminal implant comprising:
a first body including a first flange adapted to engage three sides of a first lamina end, a cantilever tab extending to a free end, and a receiving channel, the tab and receiving channel extending away from the first flange in the same direction, at least a portion of the first flange includes an opening adapted to increase pliability of the portion, provide a window through which bone growth can occur, provide for placement and securement of a bone graft, or any combination; and
a second body including a second flange adapted to engage at least two sides of a second lamina end, and a plurality of teeth adapted to engage a projection on the tab, at least a portion of the second body adapted to be positioned within the receiving channel,
the first and second bodies adapted to slideably engage one another wherein the plurality of teeth are shaped such that they can pass the tab when moving in a first direction, and are prevented from moving, by the tab, in a second direction opposite the first direction.

2. The implant of claim 1, wherein both the first and second bodies include at least one through hole.

3. The implant of claim 1, further comprising at least one pin hole on each of the first and second bodies capable of interacting with an insertion instrument.

4. The implant of claim 1, wherein the free end of the cantilever tab is biased such that as a tooth, moving in the first direction, contacts the free end, the free end deflects away from the plurality of teeth, but the free end is not deflectable when the tooth, moving in the second direction, contacts the free end.

5. The implant of claim 1, wherein the tab further includes an access port for interaction with an instrument to manually deflect the free end of the cantilever tab away from the plurality of teeth and thereby allow for movement of the teeth in the second direction, past the free end.

6. The implant of claim 1, further comprising a stop adapted to prevent the first and second bodies from disengaging one another.

7. The implant of claim 1, wherein the receiving channel limits the portion of the second body within the receiving channel to only sliding motion relative the first body.

8. The implant of claim 1, wherein the flange of the first body is larger than the flange of the second body.

9. The implant of claim 1, wherein the second body includes side rails and the receiving channel includes guide slots that are keyed to receive the side rails in a mating relationship to allow the first and second bodies to slideably engage each other.

10. A laminal implant comprising:
a first body having a flange, a deflectable cantilever tab, and a receiving channel, a first portion of the flange including an opening and a second portion of the flange including at least one through hole, the first portion of the flange adapted to be positioned on an inner side of a cut lamina end and the second portion of the flange adapted to be positioned on an outer side of the cut lamina end, the opening of the first portion includes a perimeter defined by the first portion on four sides and is adapted to increase pliability of the portion, provide a window through which bone growth can occur, provide for placement and securement of a bone graft, or any combination; and
a second body having a plurality of teeth adapted to engage the tab, at least a portion of the second body adapted to be positioned within the receiving channel such that the first and second bodies are removeably coupled to one another and slidable relative to one another such that the implant is expandable, wherein the plurality of teeth are shaped such that they can pass the tab when moving in a first direction, and are prevented from moving, by the tab, in a second direction opposite the first direction.

11. The implant of claim 10, wherein the portion of the flange of the first body having the opening is pliable.

12. The implant of claim 10, wherein as a tooth, moving in the first direction, contacts the tab, the tab deflects away from the plurality of teeth, but the tab is not deflectable when the tooth, moving in the second direction, contacts the tab.

13. The implant of claim 12, wherein the tab further includes an access port for interaction with an instrument to manually deflect the tab away from the plurality of teeth and thereby allow for movement of the teeth in the second direction, past the tab.

14. A laminal implant comprising:
a first body including a first flange adapted to engage three sides a first lamina end, a tab and a receiving channel;
a second body including a second flange adapted to engage at least two sides of a second lamina end, and a plurality of teeth adapted to engage the tab, at least a portion of the second body adapted to be positioned within the receiving channel, the first flange being larger than the second flange; and
a stop,
the first and second bodies adapted to slideably engage one another wherein the plurality of teeth are shaped such that they can pass the tab when moving in a first direction, and are prevented from moving, by the tab, in a second direction opposite the first direction, wherein the stop is adapted to prevent the first and second bodies from disengaging one another, wherein at least a portion of the first flange includes an opening adapted to increase pliability of the portion, provide a window through which bone growth can occur, provide for placement and securement of a bone graft, or any combination.

15. The implant of claim 14, further comprising at least one pin hole on each of the first and second bodies capable of interacting with an insertion instrument.

16. The implant of claim 14, wherein the tab is biased such that as a tooth, moving in the first direction, contacts the tab, the tab deflects away from the plurality of teeth, but the tab is not deflectable when the tooth, moving in the second direction, contacts the tab.

* * * * *